United States Patent [19]

Urata

[11] Patent Number: 4,690,006
[45] Date of Patent: Sep. 1, 1987

[54] JIG FOR CARRYING OUT MOVEMENT AND ALIGNMENT WITHIN A PIPE

[75] Inventor: Toshimitsu Urata, Kawasaki, Japan

[73] Assignee: Kensa Giken Co., Ltd., Kanagawa, Japan

[21] Appl. No.: 867,966

[22] Filed: May 29, 1986

[30] Foreign Application Priority Data

May 30, 1985 [JP] Japan .................................. 60-117416

[51] Int. Cl.⁴ ............................................ G01M 19/00
[52] U.S. Cl. .................................. 73/866.5; 324/220; 138/103
[58] Field of Search ............ 73/432 B, 432 G, 432 R, 73/623, 866.5, 865.8, 432.1; 138/103; 324/220; 335/219; 15/104.05, 104.09, 104.3 SN

[56] References Cited
U.S. PATENT DOCUMENTS

| | | | |
|---|---|---|---|
| 1,692,500 | 11/1928 | Gustafsson | 15/104.09 X |
| 2,158,577 | 5/1939 | Haley | 15/104.3 SN X |
| 2,308,159 | 1/1943 | Drummond et al. | 324/220 |
| 3,952,315 | 4/1976 | Cecco | 324/220 |
| 4,372,161 | 2/1983 | de Buda et al. | 73/432 G |
| 4,447,777 | 5/1984 | Sharp et al. | 324/220 |
| 4,453,410 | 6/1984 | Schmitz et al. | 73/623 X |

Primary Examiner—Tom Noland
Attorney, Agent, or Firm—Wegner & Bretschneider

[57] ABSTRACT

A jig for carrying out movement and alignment within a pipe includes a magnet having a barrel portion and magnetic pulse formed in the jig such that the jig forms part of the side of a column, a cylindrical bore formed in the barrel portion which is aligned coaxially with an axis of the column, and an instrument mounting shaft which is rotatively fitted through the cylindrical bore. The magnet may be a permanent magnet or an electromagnet. The measuring instrument can be positioned coaxially within the pipe and may be moved through a bent portion of the pipe.

11 Claims, 7 Drawing Figures

4,690,006

JIG FOR CARRYING OUT MOVEMENT AND ALIGNMENT WITHIN A PIPE

FIELD OF THE INVENTION

The present invention relates to a jig for carrying out movement and alignment within a pipe, on which an inspection instrument or cleaning apparatus is mounted and is conveniently used for moving it along and within the pipe and for aligning and securing it within the pipe for carrying out necessary operations.

BACKGROUND OF THE INVENTION

It is a matter of course that piping has become facilities which are essential for factories in various industries such as chemical and fuel industries. Recently the piping has become familiar for the civic life due to the spread of water supply, gas and central cooling and heating. Many systems including mainly pipes such as heat exchanger and boiler have been used. However many accidents have occurred due to failures of pipes. Maintenance operation such as inspection, cleaning and repair of the piping has become an essential operation for security of the civic life as well as the security of industry.

The pipings which are laid above ground and can readily be removed can be subjected to visual appearance inspection and precise inspection using various inspection instruments. However there has not been an appropriate inspection method for the piping buried underground. Conditions within the piping and decrease in wall thickness have been inspected by inserting a miniature camera or ultrasonic thickness measuring apparatus and the like into the piping portion slightly exposed above the ground. However such a method has difficulties as shown in FIGS. 4A and 4B. When the size of an inspection instrument to be inserted into the pipe is slightly smaller than the inner diameter of a pipe 2, the inspection instrument and the like 1 can be moved to a given position Q by actuating a rod 3 secured to the inspection instrument 1 from a position P, at which the inspection instrument is inserted. The relative position of the inspection instrument with respect to the pipe is not largely changed during the movement of the instrument. Accordingly, a necessary operation can be carried out at a given position if the inspection instrument has been preliminarily aligned with the pipe on insertion of the instrument. However the size of the inspection instrument should be made much smaller than the inner diameter of the pipe for passing through a bent portion such as elbow as shown in FIG. 4B if there is a bent portion between a position R where inspection is needed and a position P. In order to move the instrument, a flexible rod 4 such as a flexible spiral tube should be used in lieu of rod 3. By doing so, the relative position of the inspection instrument with respect to the pipe is largely changed so that the instrument is brought into misalignment therewith. It is also impossible to correct the misalignment from an external position of the pipe. In fact it has been impossible to carry out inspection at such a portion by means of an inspection instrument.

The size of the inspection instrument should be slightly smaller than the inner diameter of the pipe even when there is no bent portion such as elbow along the length of the pipe as shown in FIG. 4A. The precise inspection has been impossible by using an inspection instrument which requires precise alignment within a pipe.

SUMMARY OF THE INVENTION

Accordingly it is an object of the present invention to provide a guide for movement within a pipe in which disadvantages in inspection of underground buried pipe are eliminated and inspection of underground buried pipe including a bent portion can be carried out in a simple and positive manner, and in which very precise inspection can be carried out even when an inspection instrument requiring precise alignment within a pipe is used.

In one aspect of the present invention, there is provided a jig for carrying out movement and alignment within a pipe comprising a magnet including a barrel portion and magnetic poles formed in such a configuration that they form a part of the side of a column; a cylindrical bore formed in said barrel portion, said cylindrical bore being aligned coaxially with an axis of said column; and an instrument mounting shaft which is rotatably fitted through said cylindrical bore.

An electromagnet which can be magnetized or demagnetized from an external position is used as a magnet for inspecting a pipe including a bent portion. A permanent magnet, the structure and operation of which is simple is used for inspecting a pipe portion including no bent portion.

The present invention provides a jig for carrying out movement and alignment within a pipe, including a magnet, on which an inspection instrument is mounted, said jig being capable of being freely moved within the pipe and capable of precisely aligning the inspection instrument at a desired position and has following excellent advantages:

(1) Maintenance such as precise inspection and cleaning of buried pipings and heat exchangers may be accomplished.
(2) The jig of the present invention may be very effectively used for piping and the like also laid above the ground.
(3) The jig of the present invention largely contributes the security of industry and citizen.

DESCRIPTION OF THE PREFERRED EMBODIMENTS

Figure 1:
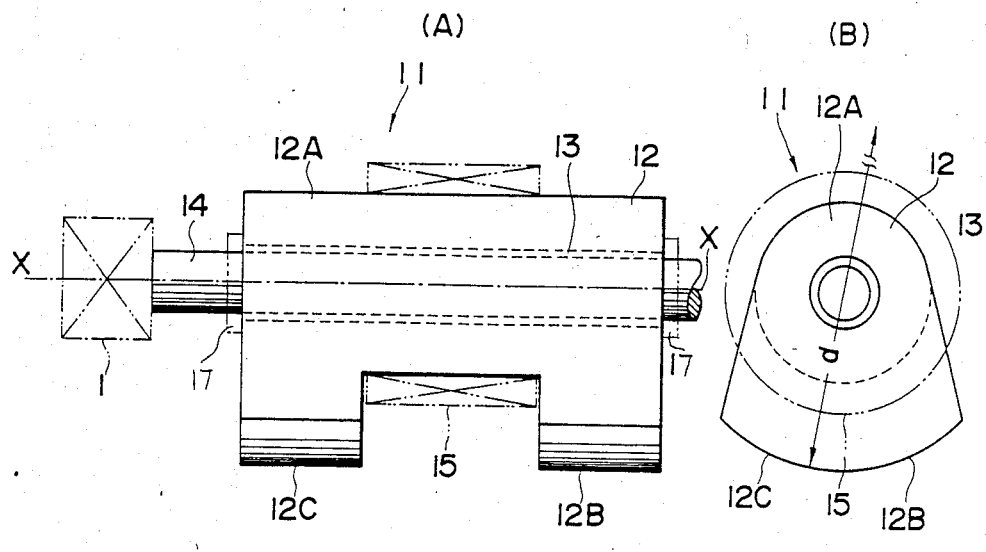
FIGS. 1(A) and 1(B) are front and right side elevational views respectively showing an embodiment of a jig for carrying out movement and alignment within a pipe in accordance with the present invention.

FIGS. 1(A) and 1(B) are front elevational and right side elevational views respectively showing a first embodiment of a jig for carrying out movement and alignment within a pipe in accordance with the present invention. As shown in these drawings the jig for carrying out movement and alignment within a pipe 11 comprises a permanent magnet 12 including a barrel portion 12A and a two magnetic pole portions 12B which is substantially U-shaped, a cylindrical sleeve 13 of a nonmagnetic material mounted within an axial cylindrical bore formed in the barrel portion 12A, and an instrument mounting shaft 14, which is rotatably fitted throughout the cylindrical sleeve 13. The outer side surface 12C of the magnetic pole portion 12B forms a part of a column having a diameter d. The cylindrical sleeve 13 is mounted so that its axis is in alignment with an axis X—X of the column. Thus the instrument mounting shaft 14 has an axis which is also in alignment with the axis X—X. An inspection instrument and the like 1 is mounted on one end of the instrument mounting shaft 14. Rotation of the instrument mounting shaft causes the inspection instrument and the like to rotate about the axis X—X. A pair of stoppers 17 may be provided on the mounting shaft 14 so as to secure the relative axial relationship between the shaft 14 and the magnet 12.

An alternative second embodient is illustrated also in FIG. 1. In the second embodiment a magnetic core 12 comprises a coil mounting portion constituting a part of the barrel portion 12A and magnetic pole portions 12B and is integrally formed of a magnetic material. A coil 15 is wound around the coil mounting portion 12A. The magnetic core 12 and coil 15 form an electric magnet. The description of the other parts is omitted since its structure is substantially identical with that of the first embodiment.

A method for inspection within a pipe using the jig for carrying out movement and alignment within the pipe in accordance with the present invention will be described below. FIGS. 2(A) and 2(B) are explanatory views of the inspection method. FIG. 2(A) is an elevational view partly in section showing that the jig for carrying out movement and alignment within a pipe is disposed within the pipe. FIG. 2(B) is a sectional view along a line B—B in FIG. 2(A). The first embodiment is first described. In the drawings, a flexible pipe 5 is mounted on an end of the jig 11 for carrying out movement and alignment within a pipe, opposite to the inspection instrument. A flexible shaft 6 is housed in the flexible pipe 5.

Figure 2:
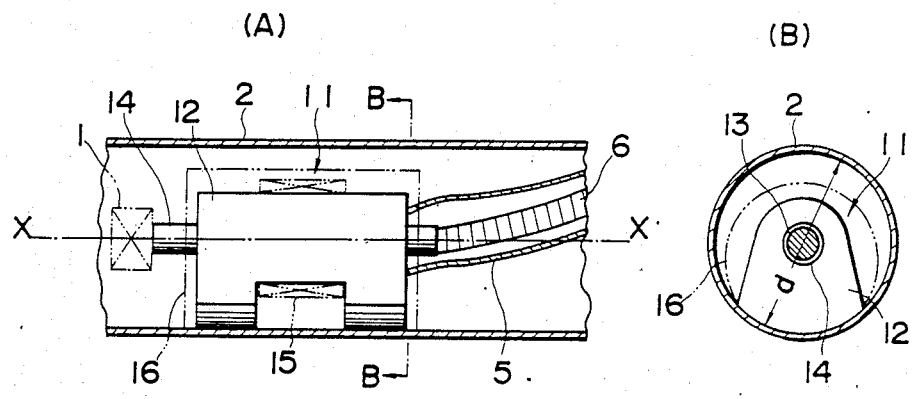
FIG. 2(A) is a front elevational view, partly in section showing a state that the jig for carrying out movement and alignment is positioned within a pipe.
FIG. 2(B) is a sectional view taken along the line B—B in FIG. 2A.
Figure 3:
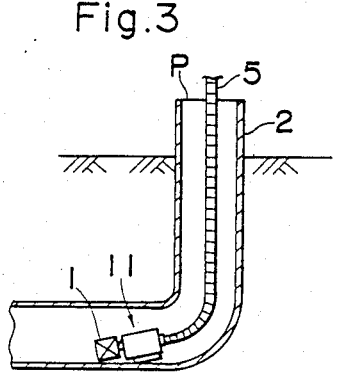
FIG. 3 is a view illustrating a method of inspection within a pipe using the jig for carrying out movement and alignment within a pipe of the present invention.

The flexible shaft 6 is secured to one end of the instrument mounting shaft 14. The jig for carrying out movement and alignment within a pipe is inserted into a pipe from the open portion P of the pipe 2 as shown in FIG. 3. Since the diameter d of the column is selected so that it is substantially the same as the inner diameter of the pipe, the size of the jig for carrying out movement and alignment within a pipe is small enough in comparison with the inner diameter of the pipe. The jig 11 can be moved to a suitable position in the pipe by operating the flexible pipe 5 (rod 3 and the like may be used) if there is no bending portion such as elbow. After having been moved to a given position, the jig 11 for carrying out movement and alignment within the pipe is secured and its axis X—X is rendered in alignment with the axis of the pipe as shown in FIG. 2 since the magnetic pole portion 12B is adhered to the wall surface when actuation of the flexible pipe 5 is stopped. Accordingly, the inspection instrument and the like 1 is brought into precise alignment within the pipe. Further, by rotating the flexible shaft 6 from the external position the inspection instrument and the like 1 is rotated around the axis of the pipe for accomplishing the operations such as inspection for entire of the inner wall of the pipe at this position.

Figure 4:
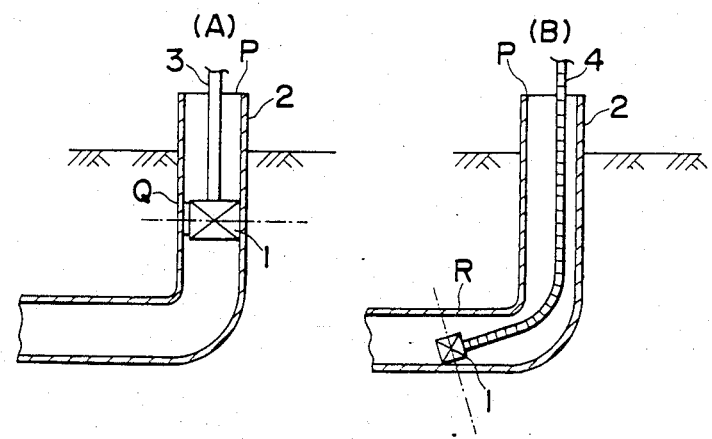
FIGS. 4(A) and 4(B) are views showing disadvantages in prior art encountered when buried underground pipes are to be inspected.

It is desired to use the aforementioned second embodiment, when there is a bend portion such as elbow etc. between a position where an inspection is to be made and a position where the inspection instrument and the like is inserted as shown in FIG. 4(B). Such a case will now be described.

In FIG. 2, the jig 11 for carrying out movement and alignment within a pipe which is shown in the second embodiment is disposed within the pipe. A conductor (not shown) which is linked with the coil 15 is housed in the flexible pipe 5. The coil 15 is not energized when the jig 11 for carrying out movement and alignment within the pipe is first inserted. Since the outer size of the jig 11 for movement and alignment within the pipe is enough small in comparison to the pipe 2, the jig 11 can easily pass through the bent portion such as elbow. When the jig 11 for carrying out movement and alignment within a pipe has reached a given position within the pipe supply of an electric current through the coil via the conductor causes the magnetic flux to be generated in the magnetic core 12 so that the magnetic pole 12B is adhered to the inner wall of the pipe 2. The inspection instrument 1 and the like is brought into precise alignment within the pipe. The inspection instrument 1 and the like is rotated about the axis of the pipe by rotating the flexible shaft 6 from an external position so that operations such as inspection may be carried out. The aforementioned operations are entirely identical with those in the first embodiment.

More precise operation could be expected if the other portion except for the outer side 12C of the core end is covered with a cover 16 of a suitable non-magnetic material when the jig 11 for carrying out movement and alignment within the shaft is used within the pipe. Although the aforementioned description has been made on the case in which the jig for movement and alignment within the pipe is mainly used for the inspection of piping and the like, the present invention may be very effectively used for the inspection of pipes of a heat exchanger and the like as well.

The pipes of heat exchanger which are made of copper or steel are widely used. The pipes made of copper may be relatively easily inspected with respect to defects by means of eddy current inspection instrument while the eddy current inspection can not be applied for the pipes made of steel since high noises are generated when steel pipes are to be inspected. Use of an ultrasonic inspection device and the like in combination with the aforementioned method enables very precise inspection.

What is claimed is:
1. A jig for carrying out movement and alignment within a pipe comprising:
a magnet including a barrel portion having a smaller diameter than the diameter of the pipe and magnetic poles radially extending from the barrel portion to form a pair of ends formed in such a configuration that the ends constitute a part of the side of an annular column having a diameter slightly smaller than that of the pipe, the pole ends circumferentially extending within a lower portion of the pipe;
a cylindrical bore formed in said barrel portion, said cylindrical bore being aligned coaxially with an axis of said column; and an instrument mounting shaft which is rotatably fitted through said cylindrical bore.

2. The jig for carrying out movement and alignment within a pipe as defined in claim 1 in which said magnet is a permanent magnet.

3. The jig for carrying out movement and alignment within a pipe as defined in claim 1 in which a coil is disposed therein and is connectable with a power source to form an electromagnet.

4. The jig for carrying out movement and alignment within a pipe as defined in claim 3 in which the magnet comprises a magnet core forming a substantially U-shaped section taken along the axis of the column, and the coil is disposed around the cylinder at and intermediate core portion of the U-shaped section.

5. The jig for carrying out movement and alignment within a pipe as defined in claim 1 in which the magnet forms a substantially U-shaped section taken along the axis of the column, said poles forming leg portions of the U-shaped section.

6. The jig for carrying out movement and alignment within a pipe as defined in claim 1 in which the instrument mounting shaft is connected to a flexible shaft for axial and rotational movement thereof.

7. The jig for carrying out movement and alignment within a pipe as defined in claim 6 in which a measuring instrument is coaxially mounted on a remote end of the instrument mounting shaft.

8. The jig for carrying out movement and alignment within a pipe as defined in claim 1 in which said instrument mounting shaft is connected with a flexible shaft extending within a flexible pipe mounted on an end of the jig.

9. The jig for carrying out movement and alignment within a pipe as defined in claim 1 in which within said cylindrical bore a sleeve is mounted for receiving said shaft therethrough.

10. The jig for carrying out movement and alignment within a pipe as defined in claim 1 in which a protective cover is applied on the barrel portion.

11. The jig for carrying out movement and alignment within a pipe as defined in claim 1, in which the pole ends circumferentially extend within a bottom portion of the pipe.

* * * * *